United States Patent [19]
LaHann

[11] Patent Number: 4,599,342
[45] Date of Patent: Jul. 8, 1986

[54] PHARMACEUTICAL PRODUCTS PROVIDING ENHANCED ANALGESIA

[75] Inventor: Thomas R. LaHann, Cleves, Ohio

[73] Assignee: The Procter & Gamble Company, Cincinnati, Ohio

[21] Appl. No.: 571,048

[22] Filed: Jan. 16, 1984

[51] Int. Cl.[4] .................. A61K 31/44; A61K 31/16; A61K 31/165

[52] U.S. Cl. .................................. 514/282; 514/627; 514/617

[58] Field of Search ...................... 424/260, 320, 324; 514/282, 613, 627, 617

[56] References Cited

U.S. PATENT DOCUMENTS

| | | | |
|---|---|---|---|
| 3,060,091 | 1/1962 | Witkin | 424/260 |
| 3,106,513 | 11/1961 | Reinhard | 424/199 |
| 3,110,650 | 11/1963 | Fischer et al. | 424/260 |
| 4,083,981 | 4/1978 | Yamamoto et al. | 424/260 |
| 4,238,508 | 12/1980 | Nelson | 424/324 |
| 4,313,958 | 2/1982 | LaHann | 424/324 |
| 4,315,936 | 2/1982 | Capetola et al. | 424/260 |
| 4,379,789 | 4/1983 | Capetola et al. | 424/260 |
| 4,401,663 | 8/1983 | Buckwalter et al. | 424/321 |
| 4,404,210 | 9/1983 | Schmidt | 424/260 |
| 4,407,804 | 10/1983 | Schmidt | 424/260 |
| 4,407,805 | 10/1983 | Schmidt | 424/260 |
| 4,424,205 | 1/1984 | LaHann et al. | 424/72 |

OTHER PUBLICATIONS

Kiernan, "A Study of Chemically Induced Acute Inflammation in the Skin of the Rat *Quart. J. Exp. Physiol.*, vol. 62, (1977), pp. 151-161.

Jansco et al., "Direct Evidence for Neurogenic Inflammation and its Prevention by Denervation and by Pretreatment with Capsaicin," *Br. J. Pharm. Chemother.* vol. 3, (1967), pp. 138-151.

Arvier et al., "Modification by Capsaicin and Compound 4/80 of Dye Leakage Induced by Irritants in the Rat," *Br. J. Pharm.*, vol. 59, (1977), pp. 61-68.

Yaksh et al., "Intrathecal Capsaicin Depletes Substance P in the Rat Spinal Core and Produces Prolonged Thermal Analgesia," *Science*, vol. 26, (1979), pp. 481-483.

Virus et al., "Pharmacologic Actions of Capsaicin: Apparent Involvement of Substance P and Serotonin," *Life Sciences*, vol. 24, (1979), pp. 1273-1281.

Goodman and Gilman, "Opioid Analgesics and Antagonists", *The Pharmacological Basis of Therapuetics*, 6th Ed., Ch. 22, (1980).

*Primary Examiner*—Stanley J. Friedman
*Assistant Examiner*—John W. Rollins
*Attorney, Agent, or Firm*—David K. Dabbiere; Steven J. Goldstein; Richard C. Witte

[57] ABSTRACT

An analgesic composition comprising capsaicin or a capsaicin analog and an analgesic selected from the class of opioids is disclosed. This combination has been found to exhibit unexpectedly enhanced analgesic activity in humans and lower animals without a corresponding increase in undesirable side effects.

25 Claims, No Drawings

PHARMACEUTICAL PRODUCTS PROVIDING ENHANCED ANALGESIA

TECHNICAL FIELD

The present invention relates to analgesic compositions comprising capsaicin or a capsaicin analog combined with a centrally-acting narcotic analgesic selected from the class of opioids. These compositions, when administered to humans or lower animals, provide a synergistic analgesic effect while minimizing undesirable side effects and toxicity.

Capsaicin and its derivatives appear to produce an analgesic effect through a mechanism largely unrelated to that of the other two categories of analgesics, and do not appear to involve the endorphin-enkephalin system, as the narcotics do. Since both capsaicin and the narcotics produce an analgesic effect, although apparently through different mechanisms, it might be expected that their combined effect would be at best additive. However, tests have shown that the analgesic effect of the combination is not merely the sum of the effects of each component, but rather an unexpected, greatly enhanced synergistic effect. Furthermore, the undesirable side effects of the two categories of analgesics are not closely related and the addition of the second analgesic does not appear to potentiate the side effects of the first. It is therefore possible to combine the two analgesics in such a dosage as to provide greatly enhanced analgesia with negligible side effects. Depending on the dosages employed, the capsaicin may either potentiate the degree of analgesia obtainable using the narcotic alone, or it may induce analgesia at dosages where no analgesic effect is obtained from either component alone.

BACKGROUND OF THE INVENTION

Traditionally, analgesics have fallen into two broad categories. Simple, non-narcotic analgesics, such as aspirin, which appear to work by inhibition of prostaglandin synthetase, are effective against pain of integumental origin such as headache and muscle aches, but are often ineffective in controlling deeper, more intense pain. The narcotic analgesics appear to work through interaction with the endorphin-enkephalin system of the central nervous system and are useful in controlling pain which is too intense to be controlled by the weaker, non-narcotic analgesics. However, centrally-acting narcotic analgesics have several serious undesirable side effects, including the development of physical dependence and tolerance, sedation, respiratory depression, hypotension, increase in cerebrospinal fluid pressure, nausea, vomiting and constipation. Therefore, it is desirable to administer the smallest effective dose possible. In some patients, particularly the chronically ill, the narcotic side effects make it impossible to administer dosages sufficient to adequately control pain over the required time period.

This invention combines capsaicin or a capsaicin derivative with a narcotic analgesic, resulting in a synergistic increase in analgesia without a corresponding increase in side effects. This makes it possible to control pain which cannot be adequately controlled by narcotics alone due to the severity of the undesirable side effects.

It has been recently discovered that capsaicin, a natural product of certain species of the genus Capsicium, induces analgesia. Capsaicin (8-methyl-N-vanillyl-6E-nonanamide) and "synthetic" capsaicin (N-vanillylnonanamide) are disclosed as analgesics in U.S. Pat. No. 4,313,958, LaHann, issued Feb. 2, 1982. Analgesic activity of capsaicin has also been discussed in the chemical and medical literature, including Yaksh, et al, *Science,* 206, pp 481–483 (1979); Jancso, et al, *Naunyn-Schmiedeberg's Arch. Pharmacol.,* Vol. 311, pp 285–288 (1980) and Holzer et al, *Eur. J. Pharm.* Vol. 58, pp 511–514 (1979). U.S. Pat. No. 4,238,505, Nelson, issued Dec. 9, 1980, discloses 3-hydroxyacetanilide for use in producing analgesia in animals. U.S. Pat. application Ser. No. 359,464, LaHann, et al, filed Mar. 18, 1982, now, U.S. Pat. No. 4,424,206, issued Jan. 3, 1984, describes hydroxyphenylacetamides with analgesic and anti-irritant activity. Similarly, analgesic and anti-irritant activity is disclosed for N-vanillylsulfonamides in U.S. Pat. No. 4,401,663, Buckwalter, et al, issued Aug. 30, 1983; N-vanillylureas in U.S. Pat. application Ser. No. 381,672, Buckwalter, et al, filed May 25, 1982, now U.S. Pat. No. 4,460,602, issued July 17, 1984; N-vanillylcarbamates in U.S. patent application Ser. No. 384,685, Buckwalter, et al, filed June 3, 1982, now U.S. Pat. No. 4,443,473, issued April 17, 1984; N-[(substituted phenyl)methyl]alkynlamides in U.S. patent application Ser. No. 514,204, Janusz, et al, filed July 14, 1983, now abandoned; methylene substituted N-[(substituted phenyl)-methyl]alkanamides in U.S. Pat. application Ser. No. 514,205, Janusz, et al, filed July 14, 1983; N[(substituted phenyl)methyl]-cis-monounsaturated alkenamides in U.S. patent application Ser. No. 514,206, LaHann, et al, filed July 14, 1983, now U.S. Pat. No. 4,498,848, issued Jan. 15, 1985; and N-[substituted phenyl)methyl]diunsaturated amides in U.S. patent application Ser. No. 514,207, LaHann, et al, filed July 14, 1983, now abandoned.

None of these references, however, suggest in any way the desirability of concurrent administration of capsaicin or a capsaicin derivative and an opioid. In fact, just the opposite is suggested. Both U.S. Pat. No. 4,313,958 (LaHann) and Yaksh et al suggest that the mechanism of capsaicin-induced analgesia is totally unrelated to that of narcotic-induced analgesia. It is extremely hard to predict when a synergistic effect will be obtained from two pharmaceutical compositions which take effect through different mechanisms. Furthermore, the only references which considered the effect of capsaicin pretreatment on morphine analgesia suggest that, when young rats are pretreated with capsaicin and then injected with morphine 1–4 months later, there is generally no effect (Holzer et al), and that in some cases pretreatment with capsaicin can in fact decrease morphine analgesia (Jancso et al).

Although there are several patents which disclose analgesic compositions containing a narcotic combined with another analgesic compound, none of these compounds has a structure at all similar to that of capsaicin. See U.S. Pat. Nos. 4,404,210, Schmidt, issued Sept. 13, 1983; 4,083,981, Yamamoto, issued April 11, 1978; 4,315,936, Capetola et al, issued Feb. 16, 1982; 4,379,789, Capetola et al, issued April 12, 1983.

Thus, based on the art, one would have expected the combination of capsaicin or a capsaicin analog with an opioid analgesic to produce no enhancement of the analgesic effect at best, and at worst, an antagonistic response. Yet, surprisingly, it has now been found that such a combination results in a synergistic increase in analgesia.

SUMMARY OF THE INVENTION

It has now been found that combinations of capsaicin derivatives of the general formula

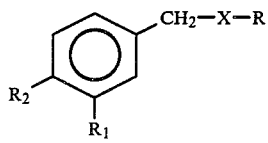

wherein $R_1$ is OH or $OCH_3$, $R_2$ is OH or a short-chain ester, ester, X is

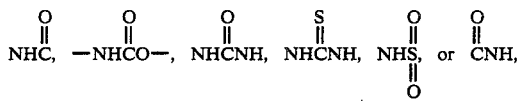

and R is a $C_5$–$C_{11}$ alkyl, $C_5$–$C_{11}$ alkenyl, $C_{11}$–$C_{23}$ cis alkenyl, $C_{11}$–$C_{23}$ alkynyl, $C_{11}$–$C_{23}$ alkadienyl, or $C_{11}$–$C_{23}$ methylene substituted alkane, with an opioid analgesic at weight ratios of capsaicinoid to opioid from about 20,000:1 to 1:20, and preferably from about 10,000:1 to 1:10, depending on the relative strength of the opioid, provide unexpectedly enhanced analgesic activity in humans and lower animals without a corresponding increase in undesirable side effects.

Another aspect of the present invention comprises the method of alleviating pain in humans and lower animals by concurrent administration of a safe and effective amount of a capsaicinoid and an opioid, as described above.

DETAILED DESCRIPTION OF THE INVENTION

A. Definitions

By the term "comprising" as used herein is meant that various other inert ingredients, compatible drugs and medicaments, and steps can be employed in the compositions and methods of the present invention as long as the critical capsaicinoid/opioid combination is present in the compositions and is used in the manner disclosed. The term "comprising" thus encompasses and includes the more restrictive terms "consisting essentially of" and "consisting of" which characterize the use of the compositions and methods disclosed herein.

By "compatible" herein is meant that the components of the composition are capable of being commingled without interacting in a manner which would substantially decrease the analgesic efficacy of the total composition under ordinary use situations.

By "administer concurrently" is meant either the administration of a single composition containing both the capsaicinoid and the opioid, or the administration of the capsaicinoid and the opioid as separate compositions within a short enough time period that the effective result is equivalent to that obtained when both compounds are administered as a single composition. Normally this would involve two separate dosages given within 10 minutes of each other. However, since many capsaicinoids retain effectiveness over unusually long time periods (possibly up to 3 days in some cases) and most opioids provide effective analgesia for relatively short time periods (4–8 hours), it may be desirable in some cases to implement a therapeutic regimen whereby each component is administered according to a schedule determined by its own period of analgesic effectiveness in order to maintain optimum effectiveness of the combination. The preferred method of administration is as a single composition.

All percentages and ratios herein are by weight unless otherwise specified.

B. Compositions

The compositions of the present invention comprise a safe and effective amount of a combination of:
(a) capsaicin or a capsaicin analog,
(b) an analgesic selected from the group of opioids, and
(c) a pharmaceutically-acceptable carrier.

A safe and effective amount of the composition is that amount which provides analgesia, thereby alleviating or preventing the pain being treated at a reasonable benefit/risk ratio, as is intended with any medical treatment. Obviously, the amount of analgesic used will vary with such factors as the particular condition that is being treated, the severity of the condition, the duration of the treatment, the physical condition of the patient, the nature of concurrent therapy (if any), the method of administration, and the specific formulation and carrier employed.

Weight ratios of capsaicinoid to opioid vary widely due to the great variation in strength among opioids. A preferred weight ratio for a capsaicinoid combined with an extremely potent opioid, such as fentanyl or etorphine, could be as high as 20,000:1, while a preferred weight ratio for a capsaicinoid combined with one of the weaker opioids, such as codeine or propoxyphene, could be as low as 1:20. Generally, weight ratios will be higher for injectable opioids than for opioids which are administered orally due to the higher potency of the injectable opioids. As a representative example, weight ratios of capsaicinoid:morphine may range from about 1200:1 to about 1:3, with preferred ranges from about 50:1 to about 1:1. Weight ratios of capsaicinoid:codeine may range from about 20:1 to about 1:10, with preferred ranges from about 7:1 to about 1:2. The ratio of capsaicinoid to opioid is also dependent upon the type and severity of the pain being treated.

By the term "capsaicin or a capsaicin analog" or "capsaicinoid" is meant a compound of the general formula

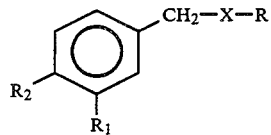

wherein $R_1$ is selected from the group consisting of OH and $OCH_3$, $R_2$ is selected from the group consisting of OH and

$R_3$ is selected from the group consisting of a $C_1$–$C_4$ alkyl, phenyl and methyl, X is selected from the group consisting of

-continued

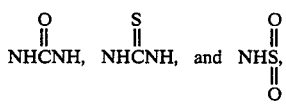

and R is selected from the group consisting of a $C_5$–$C_{11}$ alkyl, $C_5$–$C_{11}$ alkenyl, $C_{11}$–$C_{23}$ cis alkenyl, $C_{11}$–$C_{23}$ alkynyl, $C_{11}$–$C_{23}$ alkadienyl and $C_{11}$–$C_{23}$ methylene substituted alkane.

Preferred compounds include those wherein both $R_1$ and $R_2$ are OH and X is

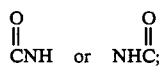

and those wherein $R_1$ is $OCH_3$, $R_2$ is OH or

Preferred R groups include $C_7$–$C_{10}$ alkyls and trans alkenyls, and $C_{16}$–$C_{21}$ cis alkenyls and alkadienyls. The preferred moieties within these groups include $C_8H_{17}$, $C_9H_{17}$ and $C_{17}H_{33}$. Preferred capsaicin analogs include N-vanillyl-alkadienamides, N-vanillyl-alkanedienyls, and N-vanillyl-cis-monounsaturated alkenamides. A particularly preferred capsaicinoid is N-vanillyl-9-octadecenamide (N-vanillyloleamide).

Preferred capsaicin analogs and methods for their preparation are described in the following U.S. Patents and Patent Applications, all incorporated by reference herein: Capsaicin (8-methyl-N-vanillyl-6E-nonenamide) and "synthetic" capsaicin (N-vanillylnonanamide) are disclosed as analgesics in U.S. Pat. No. 4,313,958, La-Hann, issued Feb. 2, 1982. European Patent Application No. 0089710, LaHann, et al, published Sept. 28, 1983, describes hydroxyphenylacetamides with analgesic and anti-irritant activity. Similarly, analgesic and anti-irritant activity is disclosed for N-vanillylsulfonamides in European Patent Application No. 0068591, Buckwalter, et al, published Jan. 5, 1983; N-vanillylureas in European patent Application No. 0068590, Buckwalter, et al, published Jan. 5, 1983; N-vanillylcarbamates in European Patent Application No. 0068592, Buckwalter, et al, published Jan. 5, 1983; N-[(substituted phenyl)methyl]alkynylamides in U.S. patent application Ser. No. 514,204, Janusz, et al, filed July 14, 1983; methylene substituted-N-[(substituted phenyl-)methyl]-alkanamides in U.S. patent application Ser. No. 514,205, Janusz, et al, filed July 14, 1983; N[(substituted phenyl)-methyl]-cis-monounsaturated alkenamides in U.S. patent application Ser. No. 514,206, LaHann, et al, filed July 14, 1983, now U.S. Pat. No. 4,498,848, issued Jan. 15, 1985; and N-[(substituted phenyl)methyl]diunsaturated amides in U.S. patent application Ser. No. 514,207, LaHann, et al, filed July 14, 1983.

By "opioid" is meant any exogenous substance which binds specifically to any of several subspecies of opioid receptors. This term is used to designate a group of drugs that are, to varying degrees, opium or morphine-like in their properties, and includes morphine, analgesic morphine derivatives and their pharmaceutically-acceptable salts, and synthetic drugs producing a morphine-like effect. The pharmacological properties and therapeutic uses of the analgesics included within the classification of opioids are described in detail in Goodman and Gilman, "Opioid Analgesics and Antagonists", *The Pharmacological Basis of Therapeutics*, 6th Ed., Ch. 22 (1980), incorporated by reference herein.

Opioids which may be utilized in the present invention include, but are not limited to, morphine, codeine, hydromorphone, oxycodone, hydrocodone, oxymorphone, propoxyphene, levorphanol, meperidine, fentamyl, methadone, pentazocine, butorphanol, and nalbuphine. Particularly preferred opioids include morphine, codeine, oxycodone, hydrocodone, fentamyl, methadone and meperidine.

By "pharmaceutically-acceptable salts" is meant those salts which are toxicologically safe for topical or systemic administration. These include phosphate, sulfate, lactate, napsylate, and hydrochloride salts.

By "pharmaceutically acceptable carrier" is meant a solid or liquid filler, diluent or encapsulating substance which may be safely used in systemic or topical administration. Depending upon the particular route of administration, a variety of pharmaceutically-acceptable carriers, well known in the art, may be used. These include solid or liquid fillers, diluents, hydrotropes, surface-active agents, and encapsulating substances. The amount of the carrier employed in conjunction with the capsaicinoid/opioid combination is sufficient to provide a practical quantity of material per unit dose of analgesic.

Pharmaceutically-acceptable carriers for systemic administration, that may be incorporated into the compositions of this invention, include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Specific pharmaceutically-acceptable carriers are described in the following U.S. Patents and Patent Applications, all incorporated by reference herein: U.S. Pat. No. 4,401,663, Buckwalter, et al, issued Aug. 30, 1983; and European Patent Application Nos. 0089710, LaHann, et al, published Sept. 28, 1983; and 0068592, Buckwalter, et al, published Jan. 5, 1983. Preferred carriers for parenteral administration include propylene glycol, ethyl oleate, pyrrolidone, aqueous ethanol, sesame oil, corn oil, and combinations thereof.

Various oral dosage forms can be used, including such solid forms as tablets, capsules, granules and bulk powders. Tablets can be compressed, tablet triturates, enteric-coated, sugar-coated, film-coated or multiple compressed, containing suitable binders, lubricants, diluents, disintegrating agents, coloring agents, flavoring agents, flow-inducing agents, and melting agents. Liquid oral dosage forms include aqueous solutions, emulsions, suspensions, non-aqueous solutions and/or suspensions reconstituted from non-effervescent granules and effervescent preparations reconstituted from effervescent granules, containing suitable solvents, preservatives, emulsifying agents, suspending agents, diluents, sweeteners, melting agents, coloring agents, and flavoring agents. Preferred carriers for oral administration include ethyl oleate, aqueous methylcellulose, gelatin, propylene glycol, cottonseed oil and sesame oil. Specific examples of pharmaceutically-acceptable carriers and excipients that may be used to formulate oral dosage forms, which may be used in formulating oral dosage forms containing monoalkenamides are described in U.S. Pat. No. 3,903,297. Robert, issued Sept.

2, 1975, incorporated by reference herein. Techniques and compositions for making solid oral dosage forms are described in Marshall, "Solid Oral Dosage Forms", *Modern Pharmaceutics*, Vol. 7, (Banker and Rhodes, editors), pp 359-427 (1979), incorporated by reference herein.

Specific systemic and topical formulations useful in this invention are described in the following U.S. Patents and Patent Applications, relating to specific capsaicin analogs and methods of treatment, which are incorporated by reference herein: U.S. Pat. No. 4,401,663, Buck walter et al, issued Aug. 30, 1983; and European Patent Application Nos. 0089710; LaHann, et al, published Sept. 28, 1983; 0068590, Buckwalter, et al, published Jan. 5, 1983; and 0068592, Buckwalter, et al, published Jan. 5, 1983. Topical vehicles, useful herein, are disclosed in the following U.S. Patent Applications, incorporated by reference herein: "Improved Penetrating Topical Pharmaceutical Compositions Combining 1-dodecylazacycloheptan-2-one", Ser. No. 506,275, Cooper, filed June 21, 1983; "Penetrating Topical Pharmaceutical Compositions Containing N-(1-hydroxyethyl)-pyrrolidone", Ser. No. 506,273, Cooper, filed June 21, 1983; "Penetrating Topical Pharmaceutical Compositions", Ser. No. 516,005, Cooper et al, filed July 20, 1983; and "Compounds Useful for Producing Analgesia", Ser. No. 514,206, LaHann and Buckwalter, filed July 14, 1983, now U.S. Pat. No. 4,498,848, issued Jan. 15, 1985.

C. Methods for Producing Analgesia

The present invention also encompasses methods for providing analgesia in humans or lower animals by administering concurrently to the human or lower animal in need of such treatment a safe and effective amount of a capsaicinoid/opioid combination or a composition containing the same. Dosages required, as well as methods of administration, are dependant on the type of opioid employed. Dosages administered may be expected to vary widely due to the wide variations in potency among the various opioids. Dosage is also dependant on the severity of the pain which must be prevented or alleviated, the physical condition of the patient, the relative severity and importance of adverse side effects, and other factors within the judgment of the physician.

The maximum dosage of the preferred capsaicin analogue vanillyloleamide (VO) which would normally be administered orally to an average adult is about 2000 mg (33 mg/kg). The minimum effective dosage is about 100 mg, (1.3 mg/kg). The maximum dosage of codeine phosphate which would normally be administered to the average adult is about 120 mg (2 mg/kg) while the minimum effective dosage is about 30 mg (0.5 mg/kg). Weight ratios of capsaicinoid to codeine may range from about 20:1 to about 1:10. Thus, the maximum allowable dosage of the combination will range from about that of codeine phosphate, 120 mg (2 mg/kg) to about that of vanillyloleamide, 2000 mg (33 mg/kg), depending on the relative proportions used. It should be noted that a sub-effective dosage of one compound may effectively potentiate the other compound; therefore, less-than-minimum dosages may be utilized in some cases. Thus, when dealing with safe and effective dosage levels of the present invention, it is more appropriate to speak of safe and effective dosages of the combination rather than of the individual components. The maximum dosage of VO which can be administered to an average adult by subcutaneous or intramuscular injection is about 400 mg (6.6 mg/kg). The maximum allowable dosage of morphine sulfate is about 30 mg (0.5 mg/kg). Weight ratios of capsaicinoid to morphine may range from about 1200:1 to about 1:3. Thus, the maximum allowable dosage will be effectively that of the capsaicinoid component, about 400 mg (6.6 mg/kg).

The compositions of this invention can be used to treat and prevent pain, and to provide analgesia in various disorders at the deeper structures, muscles, tendons, bursa and joints associated with disease and trauma, and in various other conditions in which compounds such as codeine and morphine have heretofore been used to alleviate pain and discomfort.

The compositions of the instant invention can be administered topically or systemically. Systemic application includes any method of introducing the composition into the tissues of the body, e.g., intrathecal, epidural, intramuscular, transdermal, intravenous, intraperitoneal, subcutaneous, sublingual, and oral administration.

The following non-limiting Examples illustrate the compositions, methods of treatment, and uses of the present invention.

EXAMPLE I

An analgesic composition for oral administration was made with the following proportions of the narcotic opiate codeine phosphate and the non-narcotic capsaicin analog vanillyl-9E-octadecenamide:

| | |
|---|---|
| N-vanillyl-9E-octadecenamide | 60.00 mg |
| Codeine phosphate | 18.33 mg |
| Methylcellulose | 30.00 mg |
| Saline | 6.0 ml |

The methylcellulose suspending agent and the codeine phosphate were dispersed in the saline and the octade-cenamide was suspended in the resulting solution with the aid of sonication. The preparation was dosed orally to male mice weighing approximately 25 g at a dose sufficient to deliver 30 mg/kg codeine phosphate and 100 mg/kg of the octadecenamide. Analgesic activity was demonstrated using the phenylquinone writhing test.

EXAMPLE II

An analgesic composition for oral administration was made with the following proportions of the narcotic propoxyphene hydrochloride and the non-narcotic capsaicinoid n-vanillyl-9E-octadecenamide:

| | |
|---|---|
| N-vanillyl-9E-octadecenamide | 120 mg |
| Propoxyphene HCl | 120 mg |
| Methylcellulose | 30 mg |
| Saline | 6.0 ml |

Propoxyphene was dissolved in a methylcellulosesaline mixture and the octadecenamide was then suspended in the solution by the use of sonication. The preparation was dosed orally to male mice weighing approximately 25 g at a dose sufficient to deliver 200 mg/kg propoxyphene HCl and 200 mg/kg codeine phosphate. Analgesia was demonstrated using the phenylquinone writhing test.

EXAMPLE III

An analgesic composition for intramuscular or subcutaneous injection was made using the following proportions of the narcotic opiate morphine sulfate and the non-narcotic capsaicin analog N-vanillyl-9E-octadecenamide:

| | |
|---|---|
| N-vanillyl-9E-octadecenamide | 11.3 mg |
| Morphine sulfate | 0.45 mg |
| Ethanol | 0.3 ml |
| Tween 80 | 0.3 ml |
| Saline | 2.4 ml |

The composition was made by dissolution of the morphine in the saline, dissolution of the octadecenamide in the ethanol and Tween 80 together, and admixture of the two solutions to yield a homogeneous solution containing both drugs in a final ratio of 25 part octadecenamide to 1 part morphine sulfate. 0.2 ml of the composition was injected subcutaneously into a 30 g male mouse (dosage=26 mg/kg). Analgesia was produced.

EXAMPLE IV

A composition for oral administration is made with the following components:

| | |
|---|---|
| N-vanillyl-11E-octadecenamide | 100 mg |
| Codeine phosphate | 30 mg |
| Starch | 10 mg |
| Magnesium stearate | 0.5 mg |

The above ingredients are dry-mixed and a capsule is filled with the mixture. The capsule is then administered to a 60 kg human subject, producing analgesia.

Substantially similar results are produced when the octadecenamide is replaced, in whole or in part, by capsaicin; N-vanillyl-9Z-octadecenamide; N-vanillyl-9E-octadecenamide; N-[(4-acetoxy-3-methoxyphenyl)-methyl]-9Z-octadecenamide; N-vanillyl-(Z,Z)-9,12-octadecadienamide; N-vanillyl-(E,E)-9,12-octadecadienamide; N-[(4-acetoxy-3-methoxyphenyl)-methyl]-(E,E)-9,12-octadecadienamide; N-vanillyl-(E,E)-10,13-nonadecadienamide; N-vanillyl-9-octadecynamide; 9-methylene-N-octadecanamide; 9-methylene-N-[(4-acetoxy-3-methoryphenyl)-methyl]octadecanamide; 4-acetoxy-3-methoxy-benzyl nonamide, or octyl 3,4-dehydroxyphenylacetamide. Similar results are also obtained, after adjusting the dosage to compensate for differences in the relative strength of the opioid, when the codeine is replaced, in whole or in part, by propoxyphene HCl, oxycodone, hydrocodone, dihydrocodeine, fentanyl, methadone or meperidine.

EXAMPLE V

A composition for intramuscular injection is made with the following components:

| | |
|---|---|
| N-vanillyl-9,12,15[E,E,E]-octadecatrienamide | 25 g |
| Oxycodone free base | 1 g |
| Sesame oil | 1000 ml |
| Benzyl alcohol | 15 ml |

The above ingredients are admixed by simple dissolution and 1.0 ml portions of the admixture are placed in pre-packaged sterile syringes. 1.0 ml of the composition is administered to a 70 kg human subject by intra-muscular injection, producing analgesia.

EXAMPLE VI

A composition for intramuscular administration is made with the following components:

| | |
|---|---|
| N-vanillyl-9E-octadecenamide | 25 g |
| Morphine sulfate | 1 g |
| | (26 g/100 ml carrier) |
| Carrier (percent by weight) | |
| Propylene glycol | 72% |
| Polyethylene glycol | 17% |
| Sterile water | 10% |
| Benzyl alcohol | 1% |

The composition is made by simple dissolution of the morphine sulfate in the water, simple dissolution of the octadecenamide in the propylene glycol, and admixture of the resulting solutions and other components. A 60 kg human is injected by deep intramuscular injection with 1.5 ml of the composition, producing analgesia.

EXAMPLE VII

An analgesic composition for deep intramuscular administration is made with the following ingredients:

| | |
|---|---|
| N-vanillyl-9,12[Z,Z]-octadecadienamide | 25 g |
| Merperidine HCl | 1.5 g |
| Propylene glycol | 2000 ml |
| Sterile water | 300 ml |
| Benzyl alcohol | 46 ml |

The meperidine is dissolved in the sterile water, the octadecadienamide is dissolved on the propylene glycol, and the resulting solutions are admixed with the benzyl alcohol to give a homogeneous solution. A 70 kg human subject is injected intramuscularly with 1.0 ml of this composition, producing analgesia.

Effectiveness in Providing Analgesia

1. Mouse Hot Plate Tests

The extent of analgesia obtained was determined using the mouse hot plate (MHP) analgesic model. Mice were placed one at a time on a heated copper surface ($55.0\pm0.5°$ C.) and their reactions were observed. The exposure time required to elicit either a rapid fanning or licking of any paw was used to measure the pain threshold. Analgesic effect was determined by comparing the reaction times of animals treated only with a vehicle control (typically 4.5–5.5 seconds) with the reaction times of the drug treated animals. To avoid tissue damage, rodents not responding within 60 seconds were removed from the heated surface and assigned a 60 second reaction time.

Capsaicinoids were prepared in a vehicle composed of 10% ethanol, 10% Tween 80 (polyoxyethylene (20) sorbitan mono-oleate) and 80% saline. Narcotics were dissolved in 0.9% saline. Male CF-1 mice (25–35 g) were divided into groups of 8–10, and each animal was treated with either a capsaicinoid, a narcotic analgesic, a combination of both, or the vehicle alone. All treatments were administered by subcutaneous injection. Mice receiving a combination of a capsaicinoid and a narcotic were given two separate injections within sixty seconds of each other.

The synergistic analgesic effect obtained is illustrated by, but not limited to, the following examples:

EXAMPLE VIII

Capsaicin + Morphine Sulfate

Using the procedure outlined above, groups of 10 male CF-1 mice (25–35 g) were injected subcutaneously with either the vehicle (10% ethanol, 10% Tween 80 and 80% saline) alone, 4-hydroxy-3-methoxy benzyl-nonanamide (capsaicin), morphine sulfate, or a capsaicin-morphine sulfate combination (2 separate injections within 30 seconds of each other) in the quantities shown below. Hot plate reaction times were determined at 0.5, 1, 1.5, 2, 3, and 5 hours after the injections.

| Dosage | Average Reaction Time (Seconds) | | | | | |
|---|---|---|---|---|---|---|
| | 0.5 hr. | 1 hr. | 1.5 hrs. | 2 hrs. | 3 hrs. | 5 hrs. post injection |
| MS-1 mg/kg* | 6.7 | 14.9 | 21.4 | 21.8 | 13.7 | 10.2 |
| MS-2 mg/kg | 7.2 | 21.9 | 37.4 | 36.4 | 21.7 | 22.3 |
| Cap-5 mg/kg* | 5.3 | 5.5 | 8.2 | 8.2 | 8.5 | 8.5 |
| MS-1 mg/kg + Cap-5 mg/kg | 8.4 | 23.6 | 58.4 | 56.6 | 45.0 | 19.0 |
| VC* | 5.0 | 5.0 | 5.0 | 5.0 | 5.0 | 5.0 |

*MS = morphine sulfate
Cap = capsaicin
VC = vehicle control

EXAMPLE IX

Capsaicin + Codeine Phosphate

Groups of mice were injected and their pain thresholds determined as in Example VIII, but the narcotic tested was codeine phosphate instead of morphine sulfate.

| Dosage | Average Reaction Time (seconds) | | | | | |
|---|---|---|---|---|---|---|
| | 0.5 hr. | 1 hrs. | 1.5 hrs. | 2 hrs. | 3 hrs. | 5 hrs. post injection |
| CP-13.3 mg/kg* | 8.8 | 20.4 | 32.5 | 32.5 | 29.9 | 19.2 |
| CP-26.6 mg/kg | 10.4 | 24.3 | 45.0 | 43.4 | 34.5 | 27.4 |
| Cap-5 mg/kg | 5.3 | 5.5 | 8.2 | 8.2 | 8.5 | 8.5 |
| CP 13.3 mg/kg + Cap 5 mg/kg | 8.9 | 24.6 | 60.0 | 59.4 | 55.5 | 24.7 |
| VC | 5.0 | 5.0 | 5.0 | 5.0 | 5.0 | 5.0 |

*CP = codeine phosphate

EXAMPLE X

4-Hydroxy, 3-Methoxybenzyl $\Delta_{9E}$ Octadecenamide + Morphine Sulfate

Groups of mice were injected and their pain thresholds determined as in Example VIII, but instead of capsaicin, the capsaicin analogue 4-hydroxy, 3-methoxybenzyl $\Delta_{9E}$ octadecenamide (N-vanilly-9E-octadecenamide or VO),

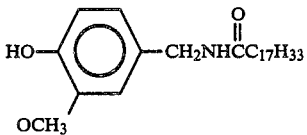

was tested.

| Dosage | Average Reaction Time (seconds) | | | | | |
|---|---|---|---|---|---|---|
| | 0.5 hr. | 1 hr. | 1.5 hrs. | 2 hrs. | 3 hrs. | 5 hrs. post injection |
| MS-1 mg/kg* | 6.7 | 14.9 | 21.4 | 21.8 | 13.7 | 10.2 |
| MS-2 mg/kg | 7.2 | 21.9 | 37.4 | 36.4 | 21.7 | 22.3 |
| VO-25* mg/kg | 5.3 | 5.5 | 7.2 | 7.3 | 7.5 | 7.5 |
| MS-1 mg/kg + VO-25 mg/kg | 8.9 | 23.2 | 53.8 | 53.3 | 46.1 | 18.0 |
| VC | 5.0 | 5.0 | 5.0 | 5.0 | 5.0 | 5.0 |

*MS = morphine sulfate
*VO = vanillyloleylamide

EXAMPLE XI

4-Hydroxy-3-Methoxy Benzyl $\Delta_{9E}$ Octadecenamide + Codeine Phosphate Groups of mice were injected and their pain thresholds determined as in Example IX but instead of capsaicin, the capsaicin analogue 4-hydroxy, 3-methoxy benzyl $\Delta_{9E}$ octadecenamide N-vanillyl- 9E-octadecenamide or VO), was tested.

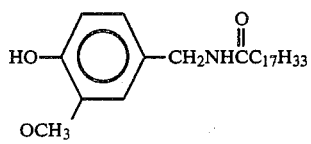

| Dosage mg/kg | Average Reaction Time (seconds) post injection | | | | | |
|---|---|---|---|---|---|---|
| | 0.5 hr. | 1 hr. | 1.5 hrs. | 2 hrs. | 3 hrs. | 5 hrs. |
| CP-13.3 mg/kg* | 8.8 | 20.4 | 32.5 | 32.5 | 29.9 | 19.2 |
| CP-26.6 mg/kg | 10.4 | 24.3 | 45.0 | 43.4 | 34.5 | 27.4 |
| VO-25 mg/kg* | 5.3 | 5.5 | 7.2 | 7.3 | 7.5 | 7.5 |
| CP-13.3 mg/kg + VO-25 mg/kg | 10.2 | 25.8 | 60.0 | 60.0 | 51.5 | 23.8 |
| VC | 5.0 | 5.0 | 5.0 | 5.0 | 5.0 | 5.0 |

*CP = codeine phosphate
VO = vanillyloleylamide

EXAMPLE XII

4-Acetoxy-3-Methoxybenzyl-nonanamide + Morphine Sulfate

Groups of mice were injected and their pain thresholds determined as in Example VIII, but instead of capsaicin, the capsaicin analogue 4-acetoxy-3-methoxy benzylnonanamide,

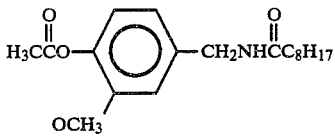

was tested.

| Dosage | Average Reaction Time (seconds) | | |
|---|---|---|---|
| | 1 hr. | 2 hrs. | 3 hrs. post injection |
| MS-20 mg/kg* | 22.1 | 16.3 | 8.5 |
| MS-20 mg/kg | 22.9 | 18.5 | 8.3 |
| MS-35 mg/kg | 49.5 | 38.3 | 12.3 |

-continued

| Dosage | Average Reaction Time (seconds) | | |
|---|---|---|---|
| | 1 hr. | 2 hrs. | 3 hrs. post injection |
| MS-35 mg/kg | 51.2 | 42.4 | 12.5 |
| MBN-25 mg/kg* | 5.7 | 5.5 | 5.2 |
| MBN-100 mg/kg | 10.4 | 8.1 | 7.8 |
| MS-20 mg/kg + MBN-25 mg/kg | 29.9 | 22.7 | 13.6 |
| MS-20 Mg/kg + MBN-100 mg/kg | 51.3 | 42.3 | 20.5 |
| MS-35 mg/kg + MBN-25 mg/kg | 55.7 | 34.4 | 13.6 |
| MS-35 mg/kg + MBN-100 mg/kg | 60.0 | 54.3 | 33.8 |
| VC | 5.0 | 5.0 | 4.9 |

*MS = morphine sulfate
MBN = 4-acetoxy-3-methoxy benzylnonanamide

2. Phenylquinon Writhing Tests

The extent of analgesia obtained was determined using the phenylquinone writhing test model. Groups of eight male mice weighing between approximately 25 and 30 g were dosed orally with the analgesic composition to be tested. Identical groups of mice were dosed with control compositions. Three hours after this initial administration, the mice were injected intraperitoneally with a 0.2% solution of phenylbenzoquinone in aqueous ethanol. The ability of the analgesic compositions tested to relieve the discomfort induced was measured by counting the number of abdominal contractions, or "writhes", occurring in each mouse during a 10 minute period beginning 10 minutes after injection of the phenylbenzoquinone solution. The results are expressed as a percent of the "writhing" response observed in the vehicle control group.

EXAMPLE XIV

An analgesic composition for oral administration was made with the following proportions of the narcotic propoxyphene hydrochloride and the non-narcotic capsaicinoid

| N-vanillyl-9-octadecenamide | 120 mg |
|---|---|
| Propoxyphene HCl | 120 mg |
| Methylcellulose | 30 mg |
| Saline | 6.0 ml |

Propoxyphene was dissolved in a methylcellulosesaline mixture and the octadecenamide was then suspended in the solution by the use of sonication. The analgesic efficacy of the combination was then contrasted with those of methylcellulose vehicle formulations lacking either the propoxyphene component, the octadecenamide component, or both. The mouse "writhing" method for assessing pain responses described above was used. The data, summarized in the following table, were normalized based on the vehicle control taken as 100.

| TREATMENT | % WRITHING RESPONSE |
|---|---|
| Methylcellulose Alone | 100 |
| Propoxyphene HCl (200 mg/kg) | 22 |
| Octadecenamide (200 mg/kg) | 34 |
| Octadecenamide (400 mg/kg) | 4 |
| Propoxyphene HCl (200 mg/kg) + Octadecenamide (200 mg/kg) | 1 |

The analgesic efficacy of this 1:1 combination of propoxyphene and vanillyl-9-octadecenamide is superior to that of either component alone as well as to that of an equal weight of octadecenamide. It is noteworthy that an equal weight dose of propoxyphene HCl (400 mg/kg) is highly toxic to mice, resulting in nacrosis and mortality.

EXAMPLE XV

An analgesic composition for oral administration was made with the following proportions of the narcotic opiate codeine phosphate and the non-narcotic capsaicin analog vanillyl-9E-octadecenamide;

| n-vanillyl-9E-octadecenamide | 60.00 mg |
|---|---|
| Codeine phosphate | 18.33 mg |
| Methylcellulose | 30.00 mg |
| Saline | 6.0 ml |

The methylcellulose suspending agent and the codeine phosphate were dispersed in the saline and the octadecenamide was suspended in the resulting solution with the aid of sonication. The preparation was dosed orally to male mice at a dose sufficient to deliver 30 mg/kg codeine phosphate and 100 mg/kg of the octadecenamide.

The analgesic activity was assessed using the "writhing" assay described above. The activity of the combination was compared with that of similar formulations lacking the codeine component, the octadecenamide component, or both.

| TREATMENT | % PAIN RESPONSE |
|---|---|
| Methylcellulose Alone | 100 |
| Codeine phosphate (30 mg/kg) | 95 |
| Octadecenamide (100 mg/kg) | 45 |
| Codeine (30 mg/kg) + Octadecenamide (100 mg/kg) | 3 |

The analgesic efficacy of this 3.33:1 combination of codeine phosphate and octadecenamide is greater than the sum of the analgesic responses of its components when given separately. This dose of codeine when given alone is not analgesic in the mouse at all. 100 mg/kg of octadecenamide produces only 55% inhibition of the pain response in this test, yet a 97% inhibition of the pain response is obtained from the combination of the two components.

EXAMPLE XVI

An analgesic composition was made comprising a mixture of codeine phosphate and vanillyl-9-octadecenamide. The formulation was similar to that of Example XV, except that twice the levels of actives were used. This formulation and the formulations for comparison are described below:

| Combination Formulation | |
|---|---|
| N—vanillyl-9-octadecenamide | 120.00 mg |
| Codeine phosphate | 36.36 mg |

| -continued | |
|---|---|
| Methylcellulose | 30.00 mg |
| Saline | 6.0 ml |
| N—vanillyl-9-octadecenamide reference formulation | |
| N—vanillyl-9-octadecenamide | 120.00 mg |
| Methylcellulose | 30.00 mg |
| Saline | 6.0 ml |
| Low dose codeine reference formulation | |
| Codeine Phosphate | 36.00 mg |
| Methylcellulose | 30.00 mg |
| Saline | 6.0 ml |
| High dose codeine reference formulation | |
| Codeine Phosphate | 120.00 mg |
| Methylcellulose | 30.00 mg |
| Saline | 6.0 ml |

Preparation of dosing forms and assay for analgesia were conducted as in Example XV:

| TREATMENT | % PAIN RESPONSE |
|---|---|
| Methylcellulose Alone | 100 |
| Codeine Phosphate (60 mg/kg) | 56 |
| Octadecenamide (200 mg/kg) | 48 |
| Codeine phophate (60 mg/kg) + Octadecenamide (200 mg/kg) | 14 |
| Codeine Phosphate (200 mg/kg) | 21 |

The 3.33:1 octadecenamide/codeine combination of Example XV is also highly effective at twice the dose. This formulation compares favorably in efficacy to a nearly equal weight oral dose of codeine. Very high oral doses of narcotics are often limited in usefulness due to constipation-producing side effects. Combination of low doses of codeine with N-vanillyl-9-octadecenamide produces efficacy equivalent to toxic narcotic doses. The octadecenamide and related capsaicin analogs do not produce opiate like side effects on the gastrointestinal tract.

Further, the combination offers additional benefits over either component alone. The slow but long acting capsaicinoid added to the rapid but short acting narcotic provides a rapid-acting, long-lasting analgesic formulation which cannot be duplicated by any single analgesic compound.

What is claimed is:

1. An analgesic composition comprising a safe and effective amount of:
   (a) an analgesic compound of the formula

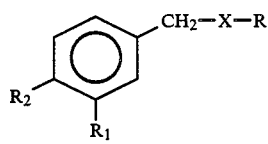

wherein $R_1$ is selected from the group consisting of OH and $OCH_3$, $R_2$ is OH, X is selected from the group consisting of

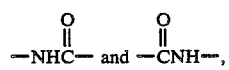

and R is selected from the group consisting of a $C_5$–$C_{11}$ alkyl, $C_5$–$C_{11}$ alkenyl, $C_{11}$–$C_{23}$ cis alkenyl, $C_{11}$–$C_{23}$ alkynyl, $C_{11}$–$C_{23}$ alkadienyl and $C_{11}$–$C_{23}$ methylene substituted alkane;

(b) an analgesic opioid selected from the group consisting of morphine, oxycodone, derivatives thereof, salts thereof and mixtures thereof; and
   (c) a pharmaceutically-acceptable carrier; wherein the weight ratio of (a):(b) is from about 20,000:1 to about 1:20.

2. A composition according to claim 1, wherein the weight ratio of (a):(b) is from about 10,000:1 to about 1:10.

3. A composition according to claim 2, wherein $R_1$ is OH.

4. A composition according to claim 3, wherein X is

and R is a $C_7$–$C_{10}$ alkyl group.

5. A composition according to claim 4, wherein R is $C_8H_{17}$.

6. A composition according to claim 2, wherein $R_1$ $R_1$ is $OCH_3$.

7. A composition according to claim 6, wherein X is

8. A composition according to claim 7, wherein R is a $C_7$–$C_{10}$ alkyl or trans alkenyl.

9. A composition according to claim 8, wherein R is $C_9H_{17}$.

10. A composition according to claim 7, wherein R is a $C_{16}$–$C_{21}$ cis alkenyl or alkadienyl.

11. A composition according to claim 10, wherein R is $C_{17}H_{33}$.

12. A composition according to claim 2, wherein the opioid is selected from the group consisting of morphine and analgesic morphine derivatives and their pharmaceutically-acceptable salts.

13. A composition according to claim 12, wherein the opiod analgesic is morphine.

14. A composition according to claim 13, wherein the weight ratio of capsaicinoid to morphine is from about 1200:1 to about 1:3.

15. A composition according to claim 14, wherein the capsaicinoid is N-vanillyl-9E-octadecenamide.

16. A composition according to claim 15, wherein the weight ratio of N-vanillyl-9E-octadecenamide to morphine is from about 50:1 to about 1:1.

17. A composition according to claim 2, wherein the opiod is oxycodone.

18. A method for providing analgesia in humans and lower animals which comprises administering concurrently to a human or lower animal in need of such treatment a safe and effective amount of:
   (a) an analgesic compound of the formula

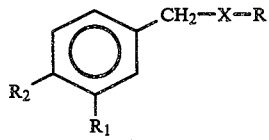

wherein $R_1$ is selected from the group consisting of OH and $OCH_3$, $R_2$ is OH, X is selected from the group consisting of

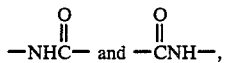

and R is selected from the group consisting of a $C_5$–$C_{11}$ alkyl, $C_5$–$C_{11}$ alkenyl, $C_{11}$–$C_{23}$ cis alkenyl, $C_{11}$–$C_{23}$ alkynyl, $C_{11}$–$C_{23}$ alkadienyl and $C_{11}$–$C_{23}$ methylene substituted alkane; and (b) an analgesic opioid selected from the group consisting of morphine, oxycodone, derivatives thereof, salts thereof and mixture thereof; wherein the weights ratio of (a):(b) is from about 20,000:1 to about 1:20.

19. A method according to claim 18, wherein R is selected from the group consisting of $C_7$–$C_{10}$ alkyl, $C_7$–$C_{10}$ trans alkenyl, $C_{17}$–$C_{21}$ cis alkenyl, and $C_{16}$–$C_{21}$ alkadienyl.

20. A method according to claim 18, wherein the capsaicinoid is N-vanillyl-9E-octadecenamide, the opioid is morphine, and the weight ratio of N-vanillyl-9E-octadecenamide to morphine is from about 50:1 to about 1:1.

21. A method according to claim 18, wherein the components are administered subcutaneously.

22. A method according to claim 18, wherein the components are administered intravenously.

23. A method according to claim 18, wherein the components are administered intramuscularly.

24. A method according to claim 18, wherein the components are administered orally.

25. A method according to claim 18, wherein the components are administered topically.

* * * * *